United States Patent
Hiramoto et al.

(10) Patent No.: US 9,757,590 B2
(45) Date of Patent: Sep. 12, 2017

(54) CHARGED PARTICLE BEAM SYSTEM

(71) Applicants: HITACHI, LTD., Tokyo (JP); NATIONAL UNIVERSITY CORPORATION HOKKAIDO UNIVERSITY, Sapporo-shi, Hokkaido (JP)

(72) Inventors: Kazuo Hiramoto, Tokyo (JP); Masumi Umezawa, Tokyo (JP); Shinichiro Fujitaka, Tokyo (JP); Hiroki Shirato, Hokkaido (JP); Shinichi Shimizu, Hokkaido (JP); Kikuo Umegaki, Hokkaido (JP)

(73) Assignees: Hitachi, Ltd., Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 14/524,495

(22) Filed: Oct. 27, 2014

(65) Prior Publication Data

US 2015/0115179 A1    Apr. 30, 2015

(30) Foreign Application Priority Data

Oct. 29, 2013    (JP) .................................. 2013-224765

(51) Int. Cl.
*A61N 5/10* (2006.01)
*A61N 5/00* (2006.01)
(Continued)

(52) U.S. Cl.
CPC ......... *A61N 5/1048* (2013.01); *A61N 5/1081* (2013.01); *G21K 1/08* (2013.01);
(Continued)

(58) Field of Classification Search
None
See application file for complete search history.

(56) References Cited

U.S. PATENT DOCUMENTS

| 6,683,318 B1 | 1/2004 | Haberer et al. |
| 2003/0141460 A1 | 7/2003 | Kraft |

(Continued)

FOREIGN PATENT DOCUMENTS

| EP | 2 400 506 A1 | 12/2011 |
| JP | 10-118204 A | 5/1998 |

(Continued)

OTHER PUBLICATIONS

Eickhoff et al., GSI Darmstadt, "Tests of a Light-Ion Gantry Scection As an Example of Preparations for the Therapy Facility in Heidelberg", Proceedings of EPAC 2002, Paris France.
(Continued)

*Primary Examiner* — Michael Logie
(74) *Attorney, Agent, or Firm* — Mattingly & Malur, PC

(57) ABSTRACT

First ions and second ions that are heavier than first ions are generated in an ion source. One kind of ions of the first ions and second ions is injected into an accelerator by action of a switching magnet and accelerated in the accelerator. An ion beam including the one kind of ions is extracted from the accelerator to a beam transport system and a tumor volume of a patient is irradiated with the ion beam from an irradiation nozzle. In the irradiation of the ion beam, a tumor volume depth and the largest underwater range of each ion species are compared, and an ion species in which the tumor volume depth becomes the longest underwater range or lower is injected into the accelerator, and accelerated by the accelerator. The tumor volume is irradiated with the ion species.

17 Claims, 8 Drawing Sheets

(51) Int. Cl.
 G21K 5/04 (2006.01)
 G21K 1/08 (2006.01)
(52) U.S. Cl.
 CPC .............. *G21K 5/04* (2013.01); *A61N 5/1043* (2013.01); *A61N 2005/1074* (2013.01); *A61N 2005/1087* (2013.01)

(56) References Cited

U.S. PATENT DOCUMENTS

| | | | | |
|---|---|---|---|---|
| 2004/0227104 A1* | 11/2004 | Matsuda | .................. | A61N 5/10 250/492.1 |
| 2008/0191142 A1* | 8/2008 | Pedroni | ................ | A61N 5/1049 250/396 ML |
| 2008/0272284 A1* | 11/2008 | Rietzel | ................... | G01T 1/169 250/252.1 |
| 2009/0101833 A1* | 4/2009 | Emhofer | .................. | A61N 5/10 250/398 |
| 2010/0320403 A1* | 12/2010 | Amaldi | .................... | A61N 5/10 250/492.3 |
| 2011/0006214 A1* | 1/2011 | Bonig | ...................... | H05H 7/18 250/396 R |
| 2011/0058750 A1* | 3/2011 | Rietzel | ................... | A61B 6/032 382/218 |
| 2011/0105821 A1* | 5/2011 | Dieter | ................. | A61N 5/1043 600/1 |
| 2012/0029862 A1* | 2/2012 | Scholz | ................. | A61N 5/1031 702/127 |
| 2012/0056109 A1* | 3/2012 | Lomax | ................. | A61N 5/1031 250/492.3 |
| 2012/0228493 A1* | 9/2012 | Gottschalk | ........... | A61N 5/1075 250/307 |
| 2013/0001432 A1* | 1/2013 | Jongen | ..................... | A61N 5/10 250/396 R |
| 2015/0057484 A1* | 2/2015 | Amaldi | .................... | H05H 7/22 600/1 |
| 2015/0133714 A1* | 5/2015 | Inaniwa | .................. | G21K 5/04 600/1 |
| 2016/0008631 A1* | 1/2016 | Harada | ................ | A61N 5/1075 600/1 |

FOREIGN PATENT DOCUMENTS

| | | | | |
|---|---|---|---|---|
| JP | 2000-354637 A | | 12/2000 | |
| JP | 2004-358237 A | | 12/2004 | |
| JP | 2009-217938 A | | 9/2009 | |
| JP | 2010-32451 A | | 2/2010 | |
| JP | 2010032451 A | * | 2/2010 | .............. G21K 5/04 |
| JP | 4632278 B2 | | 11/2010 | |
| WO | 2008/081480 A1 | | 7/2008 | |

OTHER PUBLICATIONS

Extended European Search Report received in corresponding European Application No. 14190918.4 dated Mar. 3, 2015.
Fuchs, R. et al., "The Heavy Ion Gantry of the Hicat Facility", Proceedings of EPAC 2004, Jan. 1, 2004, Lucerne, Switzerland.
Extended European Search Report received in corresponding European Application No. 15193822.2 dated Apr. 20, 2016.

* cited by examiner

ANGLE SETTING
BY ROTATING GANTRY

ANGLE SETTING
BY ROTATING GANTRY

CHARGED PARTICLE BEAM SYSTEM

CLAIM OF PRIORITY

The present application claims priority from Japanese Patent application serial no. 2013-224765, filed on Oct. 29, 2013, the content of which is hereby incorporated by reference into this application.

BACKGROUND OF THE INVENTION

Technical Field

The present invention relates to a charged particle beam system and more particularly to a charged particle beam system suitable to a cancer treatment using an ion beam such as a proton, a helium ion, or a carbon ion.

Background Art

A charged particle beam irradiation system for irradiating an ion beam such as a proton, helium, or carbon to a tumor volume of a patient to treat a cancer includes an ion source, an accelerator, a beam transport system, and a rotating gantry and the rotating gantry includes an irradiation nozzle for irradiating the ion beam to the patient.

The ion beam generated by the ion source is accelerated up to desired energy using the accelerator such as a synchrotron or a cyclotron and then is extracted from the accelerator to the beam transport system. The extracted ion beam is transported to the irradiation nozzle installed in the rotating gantry by the beam transport system. The rotating gantry is rotated, so that the irradiation nozzle is rotated around a rotation axis of the rotating gantry and is aligned with the irradiation direction of the ion beam with respect to the tumor volume of the patient on a treatment couch. Therefore, the tumor volume (the target volume) is irradiated with the ion beam transported to the irradiation nozzle in the irradiation direction set by the rotating gantry in accordance with a depth of the tumor volume, which is an irradiation target of the ion beam, from a body surface and with a shape of the tumor volume.

An ion beam irradiation method using the irradiation nozzle can be broadly divided into a scatterer method and a scanning method. In the scatterer method, the ion beam is enlarged in a lateral direction of the tumor volume, which is an irradiation target, by a scatterer, and also enlarged in a depth direction of the tumor volume by using an SOBP (spread out of Bragg peak) filter. The tumor volume is irradiated with the enlarged ion beam. In the scanning method, in accordance with the shape of the target volume, the ion beam is moved in the lateral direction of the tumor volume by using a scanning magnet and in the depth direction of it by changing the energy of the ion beam is changed by the accelerator and the whole tumor volume is irradiated with the ion beam (refer to Japanese Patent Laid-Open No. 10(1998)-118204 and Japanese Patent Laid-open No. 2004-358237).

When a human body is irradiated with the ion beam, the dose distribution as shown in FIG. 3 of Japanese Patent Laid-Open No. 10(1998)-118204 is shown in the depth direction of the human body, and the dose is maximized at the Bragg peak. Furthermore, the dose distribution reduces rapidly at a depth exceeding the Bragg peak. The cancer treatment using the ion beam uses the property that the dose is maximized at a depth exceeding the Bragg peak and the dose reduces rapidly at a depth exceeding the Bragg peak.

Japanese Patent Laid-open No. 2010-32451 describes that in one charged particle beam irradiation system, ion beams different in kind, that is, a proton ion beam (a proton beam) and a carbon ion beam (a carbon beam) are switched and the tumor volume of the patient is irradiated with the proton ion beam or the carbon ion beam. Japanese patent No. 4632278 describes that in one charged particle beam irradiation system, ion beams different in kind, that is, any of a helium ion beam, a carbon ion beam, and an oxygen ion beam is injected into the synchrotron which is an accelerator, and the injected ion beam is accelerated by the synchrotron, and then the tumor volume of the patient is irradiated with any of these accelerated beams.

H. Eickhoff et al., GSI Darmstadt, "TESTS OF A LIGHT-ION GANTRY SCECTION AS AN EXAMPLE OF PREPARATIONS FOR THE THERAPY FACILITY IN HEIDELBERG", Proc. of EPAC 2002, Paris France describes similarly to Japanese Patent Laid-open No. 2010-32451 and Japanese patent No. 4632278 that in one charged particle beam irradiation system, a plurality of kinds of ion beams are switched and an irradiation target is irradiated with the switched ion beam.

CITATION LIST

Patent Literature

[Patent Literature 1] Japanese Patent Laid-Open No. 10(1998)-118204
[Patent Literature 2] Japanese Patent Laid-open No. 2004-358237
[Patent Literature 3] Japanese patent No. 4632278

Non Patent Literature

[Non Patent Literature 1] H. Eickhoff et al., GSI Darmstadt, "TESTS OF A LIGHT-ION GANTRY SCECTION AS AN EXAMPLE OF PREPARATIONS FOR THE THERAPY FACILITY IN HEIDELBERG", Proc. of EPAC 2002, Paris France

SUMMARY OF THE INVENTION

Technical Problem

To irradiate a treatment target (a tumor volume) existing in a deep position in a body with an ion beam, an underwater range of the ion beam needs to be made long so that the ion beam arrives at an irradiation target, and as the ion weight of the ion beam is increased, higher energy is necessary. As a result, in each of the accelerator, beam transport system, and rotating gantry which are apparatuses configuring the charged particle beam irradiation system, the curvature radius of the bending magnet used needs to be large. This is related to enlargement of the size of each apparatus and as a result, the charged particle beam irradiation system is made larger.

The charged particle beam irradiation system for switching ion beams different in kind and irradiating the treatment target with one of them by the switching is structured so as to be able to irradiate it with a heaviest ion beam among those ion beams and the charged particle beam irradiation system is made larger in accordance with irradiation of the heaviest ion beam. For example, the charged particle beam irradiation system capable of performing switching between the proton ion beam and carbon ion beam and irradiating the irradiation target with one of them by the switching needs to be able to irradiate it with the carbon ion beam, so that the system is inevitably made larger.

On the other hand, in the charged particle beam irradiation system using a light ion beam like the proton ion beam, the curvature radius of the bending magnet used in the accelerator, beam transport system, and rotating gantry becomes smaller, so that the accelerator, beam transport system, rotating gantry, and irradiation nozzle can be made smaller. By doing this, the charged particle beam irradiation system using a light ion beam can downsize compared with the charged particle beam irradiation system using a heavy ion beam like the carbon ion beam.

However, the investigation of the inventors found that a problem arises that the light ion beam produces large sideward scattering by the irradiation nozzle, so that when the irradiation target is irradiated with the light ion beam, the beam size in the body increases or the dose reduction width (penumbra) at an end of the irradiation range increases, and the dose concentration to the irradiation target and the controllability of the dose distribution reduce.

An object of the present invention is to provide a charged particle beam system which can downsize and wherein irradiation concentration of ion beam to an irradiation target and controllability of irradiation dose distribution can be improved.

Solution to Problem

A feature of the present invention for attaining the above object is a charged particle beam system comprising:

an ion source generating a plurality of kinds of ions different in weight from each other;

an accelerator accelerating one kind of injected ions of the plurality of kinds of ions generated in the ion source;

a beam transport system transporting an ion beam extracted from the accelerator, the ion beam including one kind of the injected ions;

a rotating gantry setting an irradiation direction of each ion beam to an irradiation target;

an irradiation nozzle installed in the rotating gantry, the irradiation nozzle irradiating each ion beam to an irradiation target in the irradiation direction; and a control apparatus, wherein the ion source is an ion source generating a first ion and a second ion that are heavier than first ions; and wherein the control apparatus is a control apparatus executing a first control accelerating a first ion beam including the first ions by controlling frequency of high-frequency voltage applied to a high-frequency acceleration apparatus so that an underwater range of the first ion beam becomes larger than a set underwater range of a second ion beam including the second ions and the first ion beam reaches the irradiation target when water equivalent depth of the irradiation target in the irradiation direction is larger than the set underwater range of the second ion beam, and a second control accelerating the second ion beam by controlling the frequency of the high-frequency voltage applied to the high-frequency acceleration apparatus so that an underwater range of the second ion beam becomes the set underwater range of the second ion beam or smaller than the set underwater range of the second ion beam and the second ion beam reaches the irradiation target when the water equivalent depth of the irradiation target in the irradiation direction of the second ion beam is the set underwater range of the second ion beam or smaller than the set underwater range of the second ion beam.

It is preferable that the control apparatus further executes the first control to rotate the rotating gantry so that the irradiation direction of a first ion beam including the first ions from the irradiation nozzle fits to a first irradiation direction, and the second control to rotate the rotating gantry so that the irradiation direction of the second ion beam from the irradiation nozzle fits to a second irradiation direction.

(1) A charged particle beam system which is other feature of the present invention for attaining the above object comprises:

an ion source;

an accelerator accelerating ions generated in the ion source;

a beam transport system transporting an ion beam extracted from the accelerator;

a rotating gantry setting an irradiation direction of the ion beam to an irradiation target; and an irradiation nozzle installed in the rotating gantry, the irradiation nozzle irradiating the ion beam to the irradiation target in the irradiation direction, wherein the ion source is an ion source generating a plurality of kinds of ions different in weight from each other;

wherein the accelerator is an accelerator accelerating the plurality of kinds of ions so that an underwater range at highest energy after acceleration is different in an ion species; and wherein ions where a water equivalent depth (a water depth of equivalent attenuation) of the irradiation target in an irradiation direction determined by the rotating gantry is equal to an underwater range at the highest energy after the acceleration or lower are selected; and the selected ions are transported to the irradiation nozzle using the ion source, the accelerator, the beam transport system, and the rotating gantry, thereby irradiating the irradiation target with the selected ions from the irradiation nozzle.

(2) A charged particle beam system which is other feature of the present invention for attaining the above object comprises:

an ion source;

an accelerator accelerating ions generated in the ion source;

a beam transport system transporting an ion beam extracted from the accelerator;

a rotating gantry setting an irradiation direction of the ion beam to an irradiation target; and an irradiation nozzle installed in the rotating gantry, the irradiation nozzle irradiating the ion beam to the irradiation target in the irradiation direction, wherein the ion source is an ion source generating a plurality of kinds of ions different in weight from each other;

wherein the accelerator is an accelerator accelerating the plurality of kinds of ions so that an underwater range after the heaviest ion is accelerated to the highest energy becomes shorter than the underwater range after acceleration to the highest energy of ions of other than the heaviest ion; and wherein when a water equivalent depth of the irradiation target in the irradiation direction determined by the rotating gantry exceeds the longest underwater range of the heaviest ion, an ion except the heaviest ion among the plurality of ions is selected, and when the water equivalent depth of the irradiation target is equal to the longest underwater range of the heaviest ion or lower, the plurality of kinds of ions including the heaviest ion are selected, and then the selected ions are transported to the irradiation nozzle using the ion source, accelerator, beam transport system, and rotating gantry, thereby irradiating the irradiation target with the selected ions from the irradiation nozzle.

(3) A charged particle beam system which is other feature of the present invention for attaining the above object comprises:

an ion source;

an accelerator accelerating ions generated in the ion source;

a beam transport system transporting an ion beam extracted from the accelerator;

a rotating gantry setting an irradiation direction of the ion beam to an irradiation target; and an irradiation nozzle installed in the rotating gantry, the irradiation nozzle irradiating the ion beam to the irradiation target in the irradiation direction, wherein the ion source is an ion source generating a plurality of kinds of ions different in weight from each other;

wherein the accelerator is an accelerator accelerating the plurality of kinds of ions so that wherein an underwater range after acceleration of a heaviest ion to highest energy becomes shorter than an underwater range after acceleration to highest energy of ions lighter than said heaviest ion;

wherein when a water equivalent depth of the irradiation target in an irradiation direction determined by the rotating gantry exceeds a longest underwater range of the heaviest ion, ions excluding the heaviest ion among the plurality of kinds of ions are selected, and when the water equivalent depth of the irradiation target is equal to the longest underwater range of the heaviest ion or lower, the heaviest ion are selected, and then the selected ions are transported to the irradiation nozzle using the ion source, the accelerator, the beam transport system, and the rotating gantry, thereby irradiating the irradiation target with the selected ions from the irradiation nozzle.

(4) A charged particle beam system which is other feature of the present invention for attaining the above object comprises:

an ion source;

an accelerator accelerating ions generated in the ion source;

a beam transport system transporting an ion beam extracted from the accelerator;

a rotating gantry setting an irradiation direction of the ion beam to an irradiation target; and an irradiation nozzle installed in the rotating gantry, the irradiation nozzle irradiating the ion beam to the irradiation target in the irradiation direction, wherein the ion source is an ion source generating a plurality of kinds of ions different in weight from each other;

wherein the accelerator is an accelerator in which an underwater range after accelerating each of the plurality of kinds of ions to the highest energy reduces in correspondence with an increase in the ion weight; and wherein when a water equivalent depth of the irradiation target in the irradiation direction determined by the rotating gantry exceeds an underwater range at the highest energy of the heaviest ion, ions except the heaviest ion among the plurality of ions are selected, and when the water equivalent depth of the irradiation target is equal to the underwater range at the highest energy of the heaviest ion or lower, the ions included in the plurality of kinds including the heaviest ion are selected, and then the selected ions are transported to the irradiation nozzle using the ion source, accelerator, beam transport system, and rotating gantry, thereby irradiating the irradiation target with the selected ions from the irradiation nozzle.

(5) Each charged particle beam system described in the above items (1), (2), (3), and (4) comprises a control apparatus wherein the control apparatus compares the water equivalent depth of each of a plurality of layers divided in a depth direction in the irradiation target with the longest underwater range of each ion species, selects the ion species in which the underwater range corresponding to depth of the irradiation target becomes equal to the longest underwater range or lower, controls the energy of the selected ion species, thereby irradiating the irradiation target with the selected ions from the irradiation nozzle in the irradiation direction.

(6) Each charged particle beam system described in the above items (1), (2), (3), and (4) comprises a scanning magnet scanning various kinds of ions in the irradiation nozzle; and a control apparatus, wherein the control apparatus controls an irradiation position and irradiation range of the ions in a lateral direction by controlling the scanning magnet based on a position and a range in the lateral direction of each of a plurality of volume elements divided in the irradiation target, compares the water equivalent depth of each volume element in the irradiation direction determined by the rotating gantry with the longest underwater range of different ion species, selects an ion species in which the water equivalent depth of each volume element becomes equal to the longest underwater range or lower, accelerates the ion species to energy for obtaining an underwater range for irradiating each volume element, thereby irradiating each volume element with a dose determined for each volume element.

Advantageous Effect of the Invention

According to the present invention, the charged particle beam system can downsize, and the irradiation concentration of ion beam to the irradiation target is improved, and the controllability for the irradiation dose distribution in the irradiation target can be improved.

DETAILED DESCRIPTION OF THE PREFERRED EMBODIMENTS

The inventors investigated such irradiation of ion beam to an irradiation target that a charged particle beam system can be downsized and irradiation concentration of the ion beam to the irradiation target and controllability for an irradiation dose distribution can be improved. The investigation results will be explained below.

Figure 5:
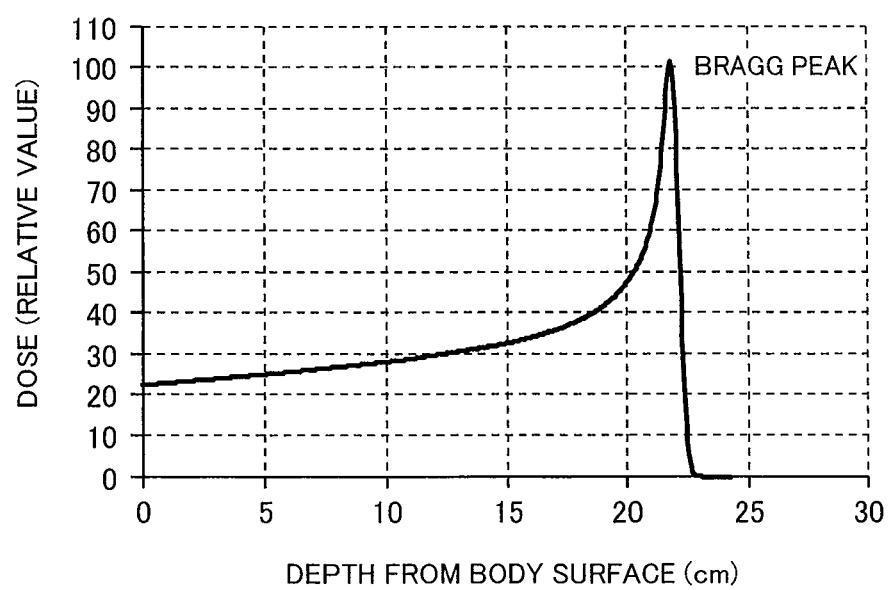
FIG. 5 is an explanatory drawing showing an example of a relative dose distribution in a depth direction in a body when an irradiation target is irradiated with an ion beam.

When a human body is irradiated with the ion beam, a dose distribution in a depth direction of the human body as shown in FIG. 5 is shown and as mentioned above, the dose is maximized at the Bragg peak. In the body, the depth that the ion beam can arrive at beyond the depth showing the Bragg peak is called a range (defined as a depth when the dose becomes 50% of dose of the Bragg peak) of the ion beam.

Figure 6:
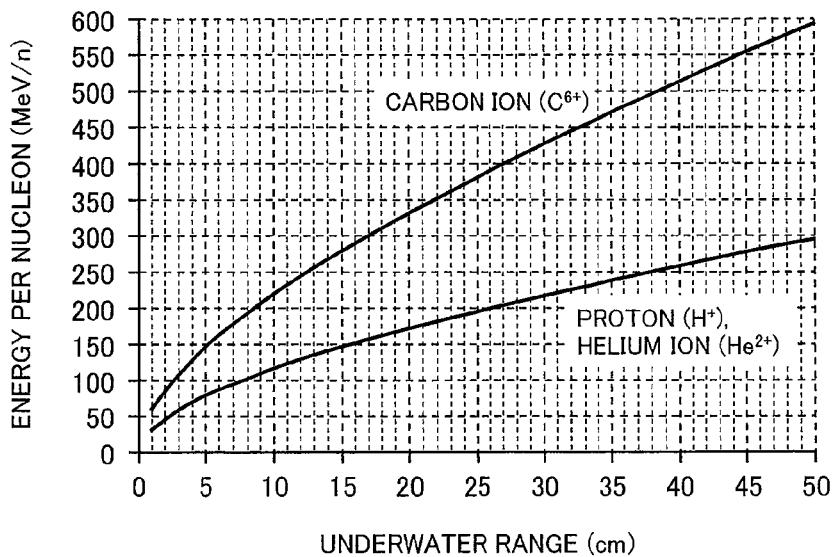
FIG. 6 is a characteristic diagram showing a relation between an underwater range of each ion in a body and energy per a nucleon of ion.

An example of a relation between an underwater range of each ion beam and kinetic energy per a nucleon on a body surface of a patient is shown in FIG. 6. For example, in a proton ($H^+$) and a helium ion ($He^{2+}$), the kinetic energy per a nucleon for obtaining the same underwater range is the same. However, in an ion heavier than the helium ion (for example, a carbon ion ($C^{6+}$)), as the mass increases, the kinetic energy necessary to increase the underwater range increases.

Figure 7:
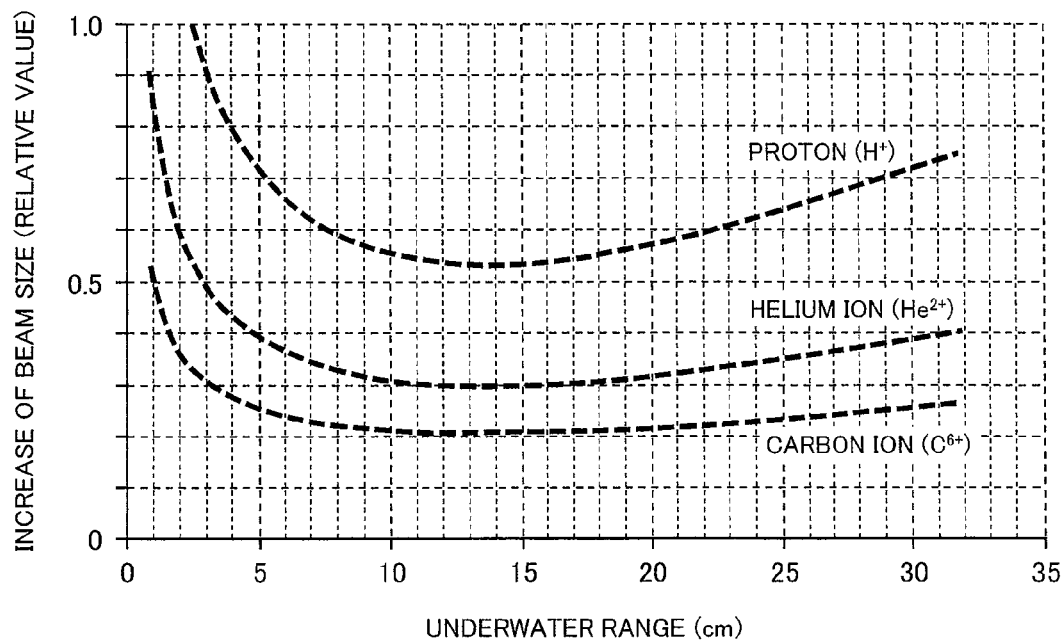
FIG. 7 is an explanatory drawing showing an example of beam size change of each ion due to an underwater range of each ion in a body.

On the other hand, in the process of irradiation of the ion beam to the irradiation target in the body from the irradiation nozzle, a beam size of the ion beam increases due to the sideward scattering by the respective materials in the irradiation nozzle and the body. The sideward scattering of the ion beam in the irradiation nozzle becomes larger as the ion beam energy becomes smaller. The sideward scattering of the ion beam by the material in the body increases in correspondence with an increase in the underwater range. As a result, the size increase in the ion beam is conspicuous in a shallow position in the body as shown in FIG. 7. Further, the size increase in the ion beam becomes smaller as the ions included in the ion beam become heavier as shown in FIG. 7.

The embodiments of the present invention reflected by the above investigation results will be explained below.

Embodiment 1

A charged particle beam irradiating method according to example 1 shown in FIG. 1 which is a preferred embodiment of the present invention will be explained by referring to FIGS. 1, 2, and 3. The charged particle beam irradiating method of the present embodiment uses the proton ion beam and helium ion beam as an ion beam with which a tumor volume which is an irradiation target is irradiated.

A charged particle beam system 5 used in the charged particle beam irradiating method of the present embodiment includes a charged particle beam generator 6, a beam transport system 21, a rotating gantry 27, an irradiation nozzle 30, and a control apparatus 33. The charged particle beam generator 6 uses a synchrotron accelerator 13 as an accelerator and as shown in FIG. 1, in addition to the synchrotron accelerator 13, includes an ion source 1 of a hydrogen molecule ($H^+$), an ion source 2 of helium ($He^{2+}$), a linear accelerator 20, and a switching magnet 3 switching the injection of hydrogen molecule ions and helium ions to the linear accelerator 20.

A beam duct (a beam path) connected to the ion source 1 with a shutter 4A installed and a beam duct connected to the ion source 2 with a shutter 4B installed are joined to each other and then are connected to the linear accelerator 20. The switching magnet 3 is disposed at the junction of the beam duct connected to the ion source 1 and the beam duct connected to the ion source 2. A charge convertor 12 is disposed between the linear accelerator 20 and the synchrotron accelerator 13, concretely, between the linear accelerator 20 and an injector 11 which will be described later.

Figure 1:
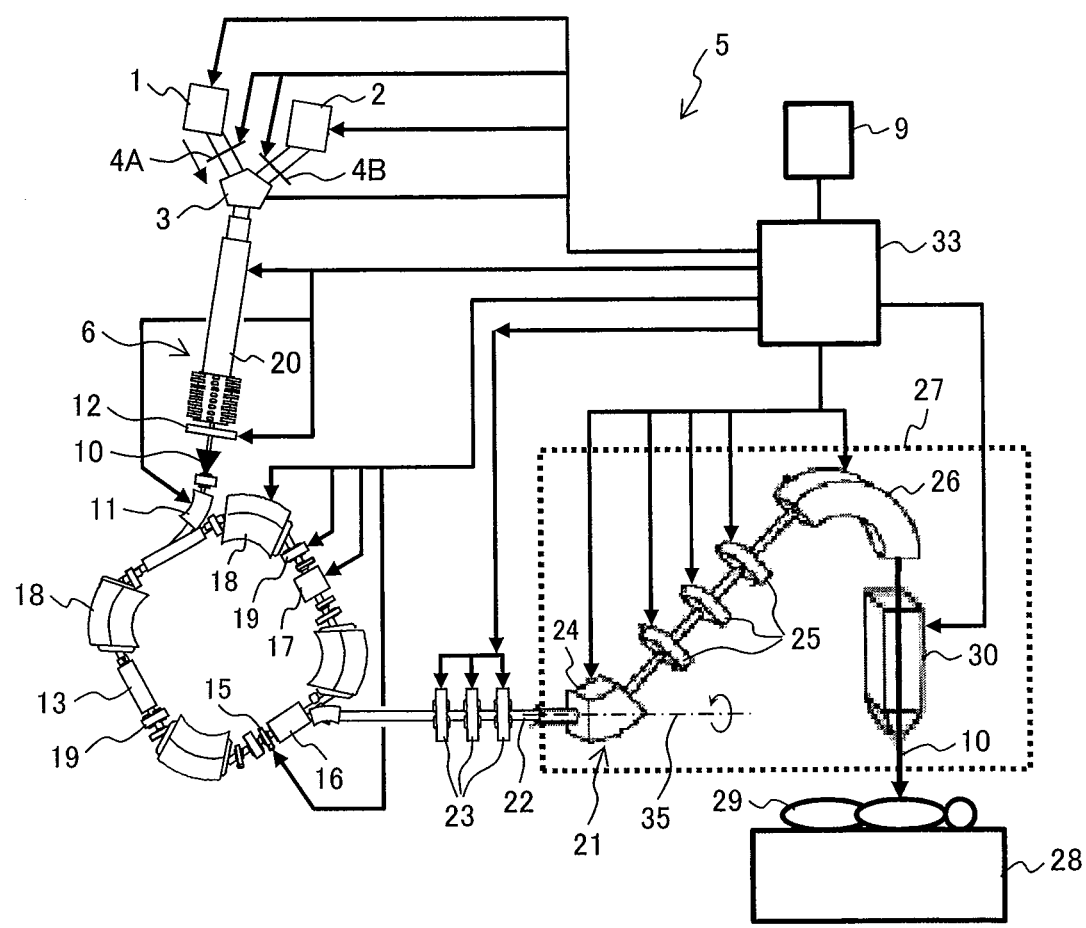
FIG. 1 is a structural diagram showing a charged particle beam system according to embodiment 1 which is a preferred embodiment of the present invention.

The synchrotron accelerator 13 is provided with a high-frequency acceleration apparatus (an acceleration cavity) 17 applying a high-frequency voltage to the ion beam, a plurality of bending magnets 18, a plurality of quadrupole magnets 19, an extraction high-frequency electrode 15, and an extraction deflector 16 on a circular beam duct and these apparatuses are arranged along the circular beam duct as shown in FIG. 1. The synchrotron accelerator 13 includes the injector 11 which is a magnet injecting the ion beam extracted from the linear accelerator 20 into the circular beam duct.

The beam transport system 21 includes a beam path 22 reaching the irradiation nozzle 30 and is structured by arranging a plurality of quadrupole magnets 23, a bending magnet 24, a plurality of quadrupole magnets 25, and a bending magnet 26 in this order on the beam path 22 and toward the irradiation nozzle 30 from the synchrotron accelerator 13. A part of the beam path 22 of the beam transport system 21 is installed on the rotating gantry 27 and the bending magnet 24, the plurality of quadrupole magnets 25, and the bending magnet 26 are also installed on the rotating gantry 27. The beam path 22 is connected to the circular beam duct of the synchrotron accelerator 13 in the neighborhood of the extraction deflector 16.

Figure 2:
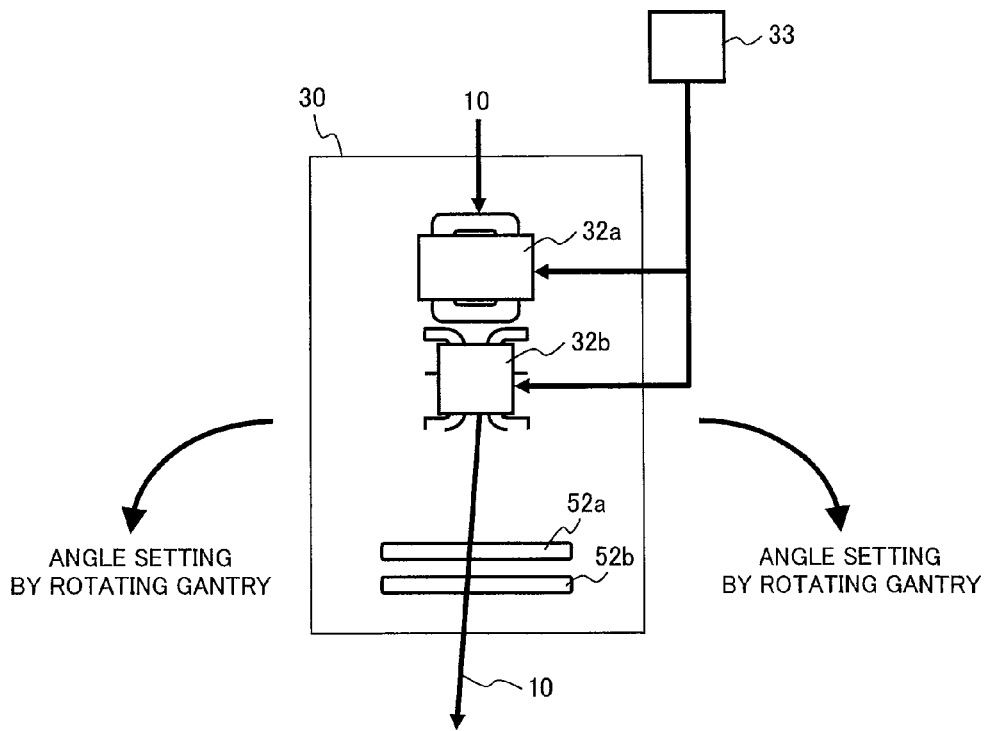
FIG. 2 is an enlarged structural diagram showing an irradiation nozzle shown in FIG. 1.

The irradiation nozzle 30 includes two scanning magnets 32a and 32b and irradiation amount monitors 52a and 52b for measuring the irradiation amount as shown in FIG. 2. The irradiation amount monitors 52a and 52b are arranged on the downstream side of the scanning magnets 32a and 32b. The irradiation nozzle 30 is attached to the rotating gantry 27 and is disposed on the downstream side of the bending magnet 26. A treatment couch 28 on which a patient 29 lies is arranged so as to be opposite to the irradiation nozzle 30.

When a tumor volume 40 of the patient 29 lying on the treatment couch 28 is irradiated with an ion beam 10, the rotating gantry 27 is rotated at a predetermined angle around a rotary shaft 35 before the irradiation of the ion beam 10, a beam axis of the irradiation nozzle 30 is adjusted to the irradiation direction of the ion beam 10 wherein the beam axis of the irradiation nozzle 30 is placed at a predetermined angle set in a treatment planning, and the beam axis of the irradiation nozzle 30 is directed to the tumor volume 40 of the patient 29 on the treatment couch 28.

The linear accelerator 20 is structured so as to be able to individually accelerate hydrogen molecule ions and helium ions, though it accelerates the hydrogen molecule ions or helium ions injected from one ion source (the ion source 1 or the ion source 2) switched by the switching magnet 3 of the two ion sources 1 and 2 at the time of irradiation of the ion beam 10. The injection of ions (the hydrogen molecule ions or helium ions) to the linear accelerator 20 from one ion source of the ion sources 1 and 2 is controlled by the switching control of the switching magnet 3 by the control apparatus 33. The beam of the hydrogen molecule ions or helium ions accelerated by the linear accelerator 20 is extracted from the linear accelerator 20 and is injected into the circular beam duct of the synchrotron accelerator 13. When the hydrogen molecule ions are accelerated by the linear accelerator 20, a charge convertor 12B is operated by the control of the control apparatus 33, and the hydrogen molecule ions extracted from the linear accelerator 20 are converted to protons by the charge convertor 12B. Therefore, the beam of the hydrogen molecule ions extracted from the linear accelerator 20 becomes a proton ion beam by the charge convertor 12B and this proton ion beam is injected into the circular beam duct of the synchrotron accelerator 13 by the injector 11.

The ion beam 10 injected into the circular beam duct is accelerated by increasing the frequency of the high-frequency voltage to be applied to a high-frequency acceleration apparatus 17 and circles in the circular beam duct which is a circular track. The high-frequency voltage is applied from a high-frequency power supply (not shown) connected to the high-frequency acceleration apparatus 17. The frequency of the high-frequency voltage to be applied to the high-frequency acceleration apparatus 17 is increased by controlling the high-frequency power supply by the control apparatus 33. When the ion beam 10 circling in the circular beam duct is accelerated, the frequency of the high-frequency voltage to be applied to the high-frequency acceleration apparatus 17 is increased and, the magnetic field strength of each bending magnet 18 and each quadrupole magnet 19 is also increased by the control of the control apparatus 33, and the energy of the ion beam 10 circling in the circular beam duct is accelerated up to predetermined energy. When the energy of the ion beam 10 which is accelerated and circles becomes the highest energy (the aforementioned predetermined energy) at the time of acceleration end, if an irradiation high-frequency voltage is applied to the extraction high-frequency electrode 15 by the control of the control apparatus 33, the irradiation high-frequency voltage is applied to the ion beam 10 circling in the circular beam duct. When the irradiation high-frequency voltage is applied to the ion beam 10, the ion beam 10 is extracted to the beam path 22 of the beam transport system 21 through the extraction deflector 16. The ion beam 10 is injected to the irradiation nozzle 30 through the beam path 22 and furthermore, the tumor volume 40 of the patient 29 on the treatment couch 28 is irradiated with the ion beam 10 from the irradiation nozzle 30. When it is extracted to the beam path 22 of the beam transport system 21 through the extraction deflector 16, the respective magnetic field strengths of each quadrupole magnet 23, the bending magnet 24, each quadrupole magnet 25, and the bending magnet 26 of the beam transport system 21 are increased so as to become equal to the magnetic field strength of each bending magnet 18 and each quadrupole magnet 19 which are adjusted when it becomes the highest energy at the time of acceleration end of the ion beam 10 circling in the circular beam duct of the synchrotron accelerator 13 by a control signal from the control apparatus 33.

In the charged particle beam irradiating method of the present embodiment, the control apparatus 33 controls respectively the scanning magnets 32a and 32b so as to scan the ion beam 10 and irradiates each spot in each divided layer of the tumor volume 40 with the ion beam 10. The irradiation of the ion beam 10 by scanning the tumor volume 40 is executed, for example, by the irradiating method described in Japanese Patent Laid-open No. 2004-358237. The change of the irradiation position of the ion beam 10 in the depth direction of the tumor volume 40 is executed by change of each of the acceleration energy of the ion beam 10 and the Bragg peak position in the depth direction caused by changing the frequency of the high-frequency voltage applied to the high-frequency acceleration apparatus 17. The change of the irradiation position of the ion beam 10 in the depth direction of the tumor volume 40 is generally executed from the distal layer toward the proximal layer.

In the present embodiment, as mentioned above, the proton ion beam and helium ion beam are used. The irradiation of the proton ion beam and helium ion beam to the tumor volume (the irradiation target) 40 of the patient 29 (refer to FIG. 3) using the charged particle beam system 5 will be explained below.

A maximum water equivalent depth of the irradiation target to be treated in the present embodiment is 30 cm, the longest underwater range of the proton ion beam (a set underwater range of a first ion beam) is set to 30 cm, and the longest underwater range of the helium ion beam (a set underwater range of a second ion beam) is set to 4 cm. When the water equivalent depth of the irradiation target is 4 cm or smaller, the irradiation target is irradiated with the helium ion beam or the proton ion beam. When the water equivalent depth of the irradiation target is between 4 cm and 30 cm, the irradiation target is irradiated with the proton ion beam from the irradiation nozzle 30. By doing this, when the water equivalent depth is 4 cm or smaller, as shown in FIG. 7, the irradiation with the ion beam in which the sideward scattering is suppressed can be executed.

When irradiating the helium ion beam to the tumor volume 40, the control apparatus 33 operates the ion source 2, opens the shutter 4B, controls the switching magnet 3, injects the helium ions generated by the ion source 2 to the linear accelerator 20, and accelerates it. At this time, the shutter 4A is closed. The helium ion beam extracted from the linear accelerator 20 is injected into the circular beam duct of the synchrotron accelerator 13 through the injector 11. When injecting the helium ion beam from the linear accelerator 20 into the circular beam duct of the synchrotron accelerator 13, the charge convertor 12 is not operated.

Figure 8:
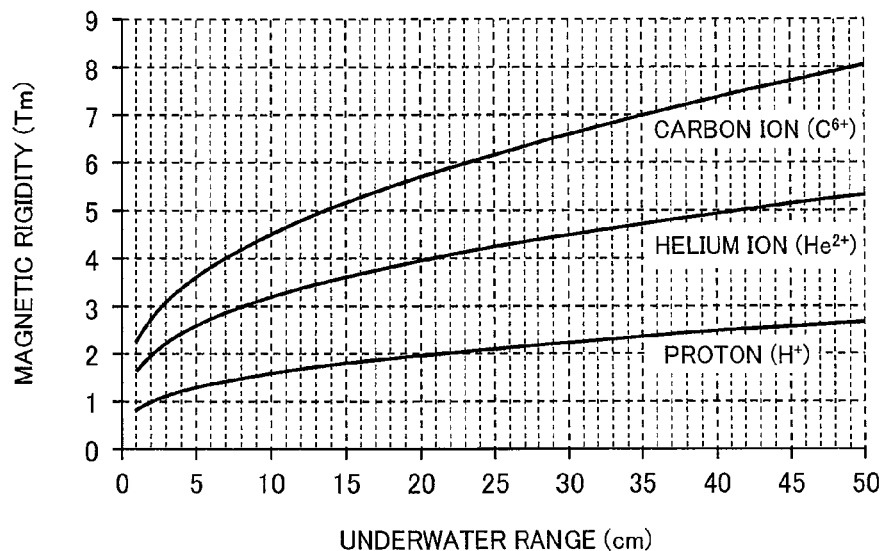
FIG. 8 is a characteristic diagram showing a relation between a magnetic rigidity of each ion and an underwater range of each ion in a body.

To obtain an underwater range of 4 cm, the helium ion beam needs to be accelerated up to 69 MeV (magnetic rigidity of 2.4) per a nucleon which is the maximum energy after the acceleration required to obtain the underwater range (refer to FIGS. 6 and 8). The magnetic rigidity is a value obtained by multiplying the radius of the circular track of the ion beam by the bending magnetic field strength. FIGS. 6 and 8 show the underwater range of the ion beam and the energy and magnetic rigidity of the ion beam required to obtain the underwater range.

To obtain a helium ion beam with an underwater range of 4 cm, the magnetic field strength of each bending magnet 18 and each quadrupole magnet 19 of the synchrotron accelerator 13 is increased based on a control signal from the control apparatus 33 so that a helium ion beam of 69 MeV per a nucleon which is the maximum energy after acceleration can circle, and furthermore, the energy of the helium ion beam is increased up to 69 MeV per a nucleon by increasing the frequency of the high-frequency voltage applied to the high-frequency acceleration apparatus 17 by the control apparatus 33. The helium ion beam is increased up to the energy necessary to reach the position of the tumor volume 40 which is irradiated with it. The respective magnetic field strengths of each quadrupole magnet 23, the bending magnet 24, each quadrupole magnet 25, and the bending magnet 26 of the beam transport system 21 are similarly controlled by the control apparatus 33 as mentioned above. The helium ion beam having energy of 69 MeV per a nucleon is extracted from the synchrotron accelerator 13 to the beam path 22 of the beam transport system 21, and the tumor volume 40 is irradiated with the helium ion beam from the irradiation nozzle 30. By the irradiation of the helium ion beam, the Bragg peak is formed in a position at a water equivalent depth of 4 cm in the depth direction from the body surface of the patient 28.

When irradiating the proton ion beam to the tumor volume 40, the control apparatus 33 operates the ion source 1, opens the shutter 4A, controls the switching magnet 3, injects the hydrogen molecule ions generated by the ion source 1 to the linear accelerator 20. The injected hydrogen molecule ions are accelerated by the linear accelerator 20. At this time, the shutter 4B is closed. The hydrogen molecule ion beam extracted from the linear accelerator 20 becomes a proton ion beam by the charge convertor 12 as mentioned above and is injected into the circular beam duct of the synchrotron accelerator 13 through the injector 11. When injecting the hydrogen molecule ion beam from the linear accelerator 20 into the circular duct of the synchrotron accelerator 13, the charge convertor 12 is operated as mentioned above.

In order to obtain an underwater range of 30 cm, the proton ion beam needs to be accelerated up to about 220 MeV (magnetic rigidity of 2.3) which is the maximum energy after the acceleration required to obtain the underwater range (refer to FIGS. 6 and 8).

To obtain a proton ion beam of an underwater range of 30 cm, the magnetic field strength of each bending magnet 18 and each quadrupole magnet 19 of the synchrotron accelerator 13 is increased based on the control signal from the control apparatus 33 so that the proton ion beam of 220 MeV which is the maximum energy after acceleration can circle, and the energy of the proton ion beam is increased up to about 220 MeV by increasing the frequency of the high-frequency voltage applied to the high-frequency acceleration apparatus 17 by the control apparatus 33. That is, the energy of the proton ion beam is increased up to the energy necessary to reach the position of the tumor volume 40 which is irradiated with the proton ion beam. The respective magnetic field strengths of each quadrupole magnet 23, the bending magnet 24, each quadrupole magnet 25, and the bending magnet 26 of the beam transport system 21 are similarly controlled by the control apparatus 33 as mentioned above. The proton ion beam having energy of about 220 MeV is extracted from the synchrotron accelerator 13 to the beam path 22 of the beam transport system 21, and the tumor volume 40 is irradiated with this proton ion beam from the irradiation nozzle 30. A Bragg peak is formed in a position at a water equivalent depth of 30 cm in the depth direction from the body surface of the patient 28 by the irradiation of the proton ion beam.

The irradiation amount monitors 52a and 52b can successively confirm the irradiation amount to the tumor volume 40 by the helium ion beam or the proton ion beam which are scanned by the scanning magnets 32a and 32b and the tumor volume 40 is irradiated with the helium ion beam or the proton ion beam.

The irradiation to the tumor volume 40 in a lateral direction (a direction perpendicular to a beam axis of the irradiation nozzle 30) by the helium ion beam and the irradiation in the depth direction can be executed by the scanning of the helium ion beam by the scanning magnets 32a and 32b and the change of the acceleration energy of the helium ion beam. Further, the irradiation to the tumor volume 40 in the lateral direction by the proton ion beam and the irradiation in the depth direction can be executed by the scanning of the proton ion beam by the scanning magnets 32a and 32b and the change of the acceleration energy of the proton ion beam.

The magnetic rigidity for accelerating the proton ion beam up to about 220 MeV which is the maximum energy and the magnetic rigidity for accelerating the helium ion beam up to 69 MeV per a nucleon which is the maximum energy are almost equal to each other and are about ½ of the magnetic rigidity for obtaining an underwater range of 30 cm of the helium ion beam.

In the present embodiment, the radius of curvature of each bending magnet used in the synchrotron accelerator 13 and the beam transport system 21 can be suppressed compared with the case that the irradiation target is always irradiated with the helium ion beam (the maximum magnetic rigidity of 4.5) until the water equivalent depth of the irradiation target becomes 30 cm and as a result, the size of each bending magnet can downsize. Therefore, the size of the charged particle beam system 5 can downsize to about ½ or the magnetic field strength of those bending magnets can be suppressed to ½.

Figure 3:
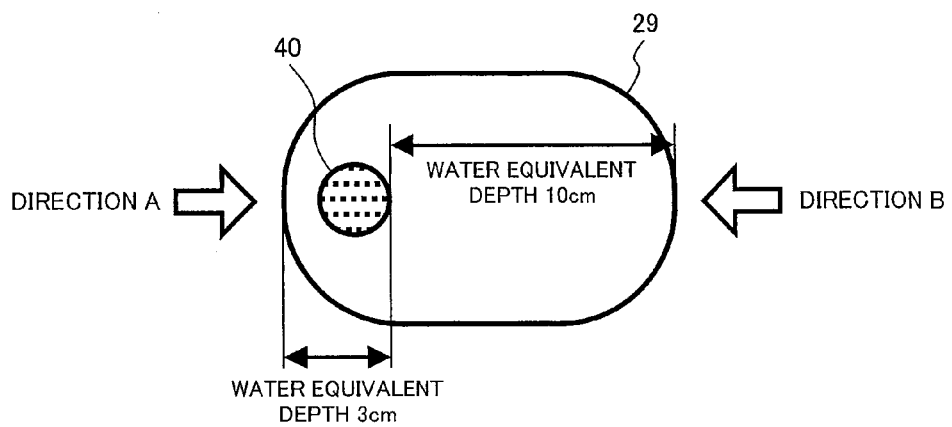
FIG. 3 is an explanatory drawing showing a state where an irradiation target is irradiated with ion beams in a charged particle beam irradiating method in which a charged particle beam system shown in FIG. 1 is used.
Figure 4:
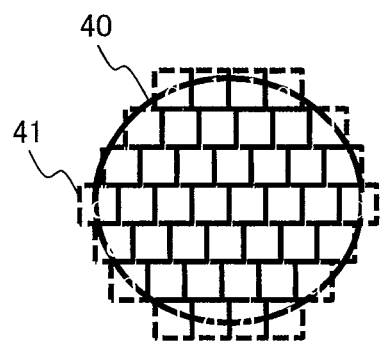
FIG. 4 is an explanatory drawing showing volume division in an irradiation target shown in FIG. 3.

FIG. 3 shows an example of a tumor volume 40 of the patient 29 which is irradiated with the helium ion beam and proton ion beam. The irradiation of the proton ion beam and helium ion beam to the tumor volume (the irradiation target) 40 of the patient 29 using the charged particle beam system 5 will be explained below. The tumor volume 40 which is an irradiation target is divided imaginarily into a plurality of volume elements 41 by the treatment planning using a treatment planning apparatus 9, as shown in FIG. 4. The irradiation direction of the ion beam, kind of the irradiated ion beam, energy of the irradiated ion beam, and irradiation amount of ion beam are determined for each volume element 41. These information is input from the treatment planning apparatus 9 to the control apparatus 33 as treatment planning information before start of the ion beam irradiation and is stored in a memory (not shown) of the control apparatus 33.

In the present embodiment, as shown in FIG. 3, the rotation angle of the rotating gantry 27 is controlled by the control apparatus 33 and the tumor volume 40 is irradiated with the ion beam in the direction A and direction B. In the ion beam irradiation in the direction A, the water equivalent depth of the entire tumor volume 40 is 3 cm, which is lower than the underwater range of 4 cm from the body surface of the patient 29, and all the volume elements 41 are is irradiated with the helium ion beam. The helium ion beam is accelerated by the synchrotron accelerator 13 up to the energy after end of the acceleration capable of obtaining the underwater range suitable for each volume element 41 and is extracted to the beam path 22 of the beam transport system 21 after the acceleration. The rotating gantry 27 is rotated and the beam axis of the irradiation nozzle 30 is beforehand fitted to the direction A. The irradiation position of the helium ion beam in the lateral direction is set by the scanning of the helium ion beam by the scanning magnets 32a and 32b of the irradiation nozzle 30 and the volume elements 41 is irradiated with the helium ion beam until a dose of each volume element 41 becomes a planned dose amount. After the irradiation of the helium ion beam of the planned amount is confirmed by the irradiation amount monitors 52a and 52b, the irradiation of the helium ion beam to the volume elements 41 is stopped. Next, when the water equivalent depth of the volume element 41 which is irradiated with the helium ion beam is the same, the magnetic field strength of the scanning magnets 32a and 32b is changed and the next volume element 41 is irradiated with the helium ion beam. When the water equivalent depth of the volume element 41 is different, the acceleration energy of the helium ion beam is changed using the high-frequency acceleration apparatus 17 so that the underwater range of the irradiated helium ion becomes a value suitable for the water equivalent depth, and the irradiation position in the lateral direction is set by controlling the magnetic field of the scanning magnets 32a and 32b and the irradiation of the helium ion beam to the applicable volume element 41 is executed. Such irradiation of the helium ion beam is executed repeatedly and the irradiation of the helium ion beam in a predetermined amount is executed to the volume elements 41 of the entire tumor volume 40.

After end of the irradiation of the helium ion beam in the direction A, the rotation angle of the rotating gantry 30 is changed and the beam axis of the irradiation nozzle 30 is fitted to the direction B. In the irradiation of the ion beam in the direction B, as shown in FIG. 3, the tumor volume 40 which is an irradiation target is located in a deeper position than an underwater range of 4 cm. Therefore, the irradiation of the proton ion beam is executed to all the volume elements 41 in the direction B. The irradiation procedure of the proton ion beam to each volume element 41 is the same as the case of the irradiation using the helium ion beam in the direction A.

In the present embodiment, the irradiation of the helium ion beam in the direction A and the irradiation of the proton ion beam in the direction B, that is, the irradiation of an ion beam to the tumor volume 40 in different directions are executed, so that the dosage irradiated to healthy cells on the foreside of the tumor volume 40 is reduced. The tumor volume 40 is irradiated with the helium ion beam in the direction A until a dose of the tumor volume 40 becomes the above dose in a predetermined amount in the direction A, and the tumor volume 40 is irradiated with the proton ion beam in the direction B until a dose of the tumor volume 40 becomes other dose in a predetermined amount in the direction B.

In the present embodiment, the tumor volume 40 is irradiated with the helium ion beam in the proximal water equivalent depth direction from the body surface of the patient 29 (for example, in the direction A giving a water equivalent depth of 3 cm) and the tumor volume 40 is irradiated with the helium ion beam in the distal water equivalent depth direction from the body surface of the patient 29 (for example, in the direction B giving a water equivalent depth of 10 cm or more), so that the bending magnets 18, 24, and 26 can downsize and the size of the charged particle beam system 5 can be made small.

Further, the tumor volume 40 is irradiated with the helium ion beam in the direction A and the tumor volume 40 is irradiated with the proton ion beam in the direction B, so that an increase in the respective beam sizes of the helium ion beam and the proton ion beam can be suppressed and the irradiation concentration of each ion beam to the tumor volume 40 can be enhanced. Furthermore, the irradiation of the helium ion beam to the tumor volume 40 in the direction A and the irradiation of the proton ion beam to the tumor volume 40 in the direction B can enhance the controllability of the irradiation dose distribution in the tumor volume 40.

In the present embodiment, the change of ion beams different in the ion species can be executed in a short period of time, so that two ion sources are used, though the ion generation gas is changed by one ion source, and a plurality of kinds of ion beams separately including ions different in weight are generated, and the irradiation target can be irradiated with the respective ion beams.

Embodiment 2

A charged particle beam irradiating method according to embodiment 2 which is another preferred embodiment of the present invention will be explained below. In the charged particle beam irradiating method of the present embodiment, the same charged particle beam system 5 used in embodiment 1 is used.

Figure 9:
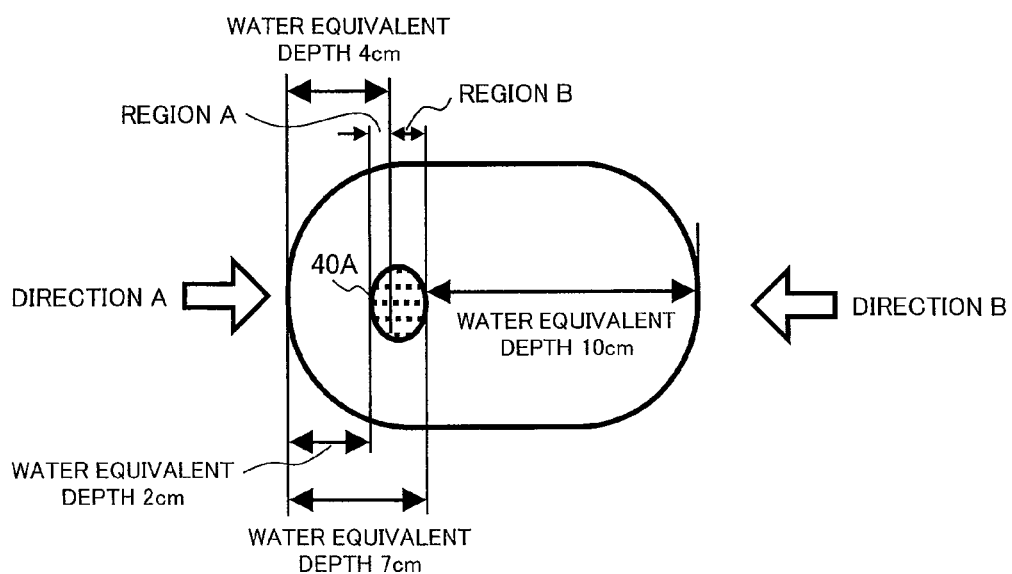
FIG. 9 is an explanatory drawing showing a state where an irradiation target is irradiated with ion beams in a charged particle beam irradiating method according to embodiment 2 which is another preferred embodiment of the present invention, the charged particle beam irradiating method using a charged particle beam system shown in FIG. 1.

FIG. 9 shows an example of the tumor volume 40 of the patient 29 which is irradiated with the helium ion beam and proton ion beam. The irradiation of the proton ion beam and helium ion beam to the tumor volume (the irradiation target) 40A of the patient 29 using the charged particle beam system 5 will be explained below. A tumor volume 40A which is an irradiation target is positioned between the water equivalent depths of 2 cm and 7 cm from the body surface of the patient 28 in the direction A and in the direction B, the water equivalent depth of the tumor volume 40A from the body surface of the patient 28 exists in a deeper position than an underwater range of 4 cm of the helium ion beam (a set underwater range of a second ion beam). Similarly to embodiment 1, when the tumor volume 40 is divided by the plurality of volume elements 41, the beam axis of the irradiation nozzle 30 is fitted to the direction A, and the irradiation of the ion beam is executed in the direction A, each volume element 41 of the tumor volume 40 existing in a position where the water equivalent depth from the body surface is 4 cm or shallower is irradiated with the helium ion beam, and furthermore, each volume element 41 of the tumor volume 40 existing in a position where the water equivalent depth from the body surface is deeper than 4 cm is irradiated with the proton ion beam. Further, when the beam axis of the irradiation nozzle 30 is fitted to the direction B and the irradiation of the ion beam is executed in the direction B, all the volume elements 41 exist in a position where the water equivalent depth from the body surface is 10 cm or more, so that all the volume elements 41 is irradiated with the proton ion beam.

Also in the present embodiment, the tumor volume 40 is irradiated with the ion beam from each of the directions A and B similarly to embodiment 1, so that the dosage irradiated to healthy cells on the foreside of the tumor volume 40 is reduced. The tumor volume 40 is irradiated with a dose in a predetermined amount by each irradiation of the helium ion beam and proton ion beam in the direction A and the irradiation of the proton ion beam in the direction B. When the volume elements exist in a position deeper than an underwater range of 4 cm, the volume elements are irradiated with the proton ion beam, and when the volume elements exist in a position of an underwater range of 4 cm or shallower, the volume elements are irradiated with the helium ion beam.

The present embodiment can improve the irradiation concentration to the tumor volume 40 and the controllability of the irradiation dose distribution, similarly to embodiment 1. Particularly, in the present embodiment, all the volume elements existing in the region A where the depth from the body surface is a water equivalent depth of 4 cm or lower are irradiated with the helium ion beam, though all the volume elements existing in the region B exceeding a water equivalent depth of 4 cm are irradiated with the proton ion beam. In this way, in the irradiation of the ion beam from the direction A, the controllability of the dose distribution can be further improved in a combination of the volume elements which are irradiated with the helium ion beam and the volume elements which are irradiated with the proton ion beam. Further, the region A is irradiated with the helium ion beam having a small beam size and the region B is irradiated with the proton ion beam having a relatively large beam size, so that the irradiation can be finished in a short period of time by improving the dose concentration to the irradiation target.

Embodiment 3

Figure 10:
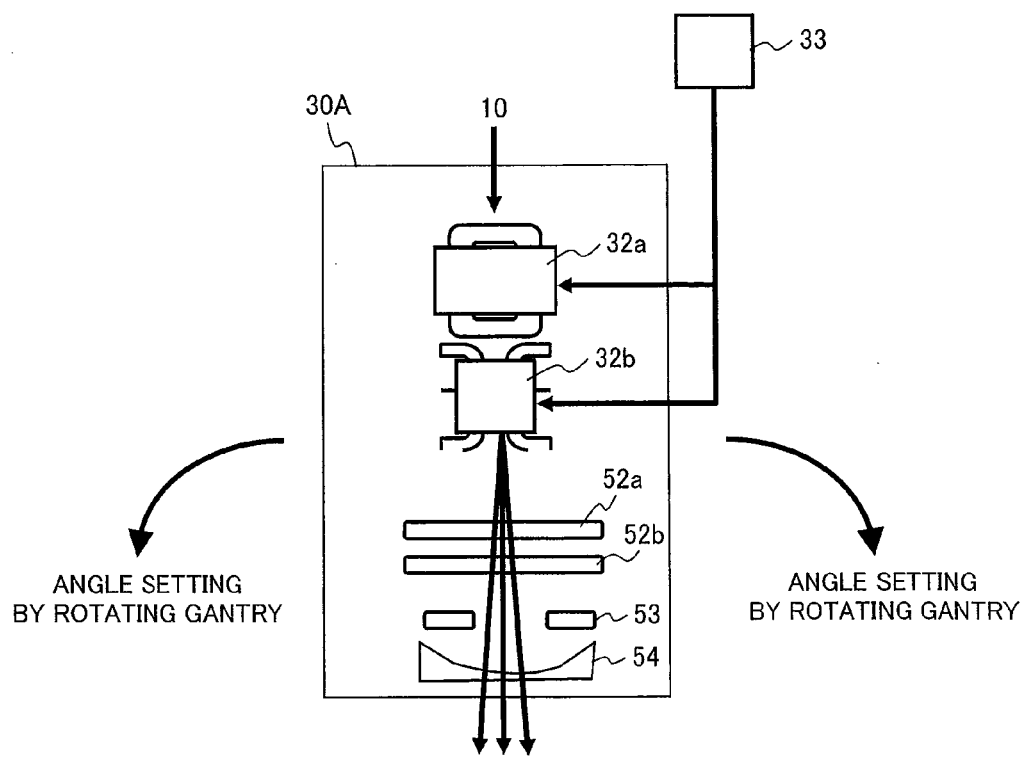
FIG. 10 is an enlarged structural diagram showing an irradiation nozzle of a charged particle beam system according to embodiment 3 which is other preferred embodiment of the present invention.

The charged particle beam irradiating method according to embodiment 3 which is other preferred embodiment of the present invention will be explained below. In the charged particle beam irradiating method of the present embodiment, a charged particle beam system having an irradiation nozzle 30A shown in FIG. 10 as a substitute for the irradiation nozzle 30 in the charged particle beam system 5 used in embodiment 1, is used. A structure of the charged particle beam system except the irradiation nozzle 30A used in the present embodiment is the same as that of the charged particle beam system 5.

The scanning magnets 32a and 32b, the irradiation amount monitors 52a and 52b for measuring the irradiation amount, and a collimator 53 for determining the radiation field range in the lateral direction are installed in the irradiation nozzle 30A. Further, a range compensator 54 compensating the underwater range based on the shape of the irradiation target in the depth direction is installed in the lower part of the irradiation nozzle 30. The other structure of the charged particle beam system of the present embodiment is the same as the structure shown in FIG. 1. Also in the present embodiment, the proton ions and helium ions are used, the proton ions are accelerated up to the energy of the underwater range of 30 cm and the helium ions are accelerated up to the energy of the underwater range of 4 cm. The ion beam extracted from the synchrotron accelerator 13 is transported to the irradiation nozzle 30 installed in the rotating gantry 31 by the beam transport system 14.

Figure 11:
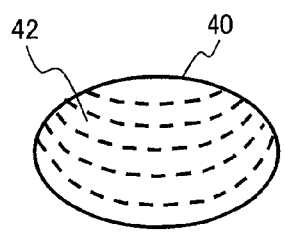
FIG. 11 is an explanatory drawing showing layer division in an irradiation target which is irradiated with ion beam from an irradiation nozzle of a charged particle beam system shown in FIG. 10.

In the present embodiment, the tumor volume 40 is divided into a plurality of layers 42 in the depth direction as shown in FIG. 11. When the water equivalent depth of each layer adjusted to the range change by the range compensator is 4 cm or lower, each layer is irradiated with the helium ion beam and when it of each layer exceeds 4 cm, each layer is irradiated with the proton ion beam.

Figure 14:
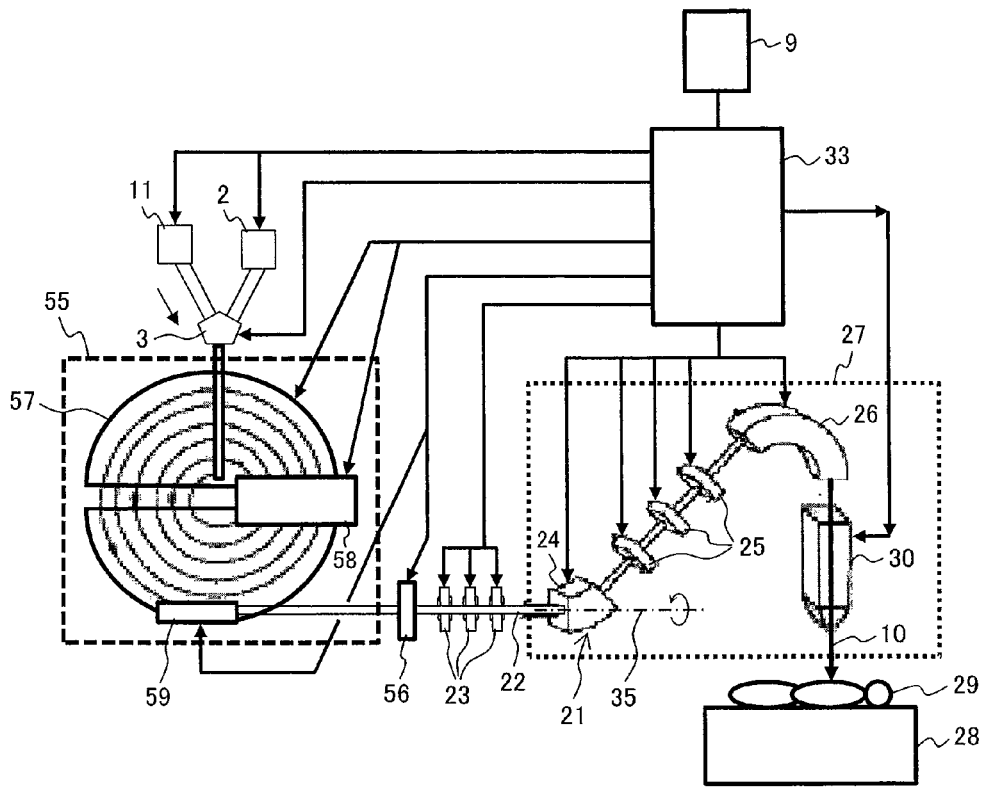
FIG. 14 is a structural diagram showing a charged particle beam system which is other preferred embodiment of the present invention.

In the present embodiment, the linear accelerator 12 and the synchrotron accelerator 13 are used as an accelerator, though as shown in FIG. 14, a cyclotron accelerator 55 for extracting the proton ($H^+$) ion beam and helium ($He^{2+}$) ion beam at fixed energy is used as an accelerator, and a metallic degrader 56 for permitting the ion beam to pass through is installed in the beam transport system, and the attenuation amount of the ion beam energy is controlled by changing the thickness of the degrader is changed. Thus, a similar system to each of embodiments 1 to 3 can be realized by using the cyclotron accelerator 55.

When switching the proton ions and helium ions, the polarity of the switching magnet 3 shown in FIG. 14 is changed, and the magnetic field of a bending magnet 57 of the cyclotron accelerator 55, the resonance frequency control of a high-frequency accelerator 58, and the applied high-frequency and the voltage applied to an irradiation deflector 59 are changed and controlled. As a consequence, the proton ions or helium ions is accelerated and each layer in the tumor volume 40 is irradiated with the proton ions or helium ions.

Embodiment 4

Figure 12:
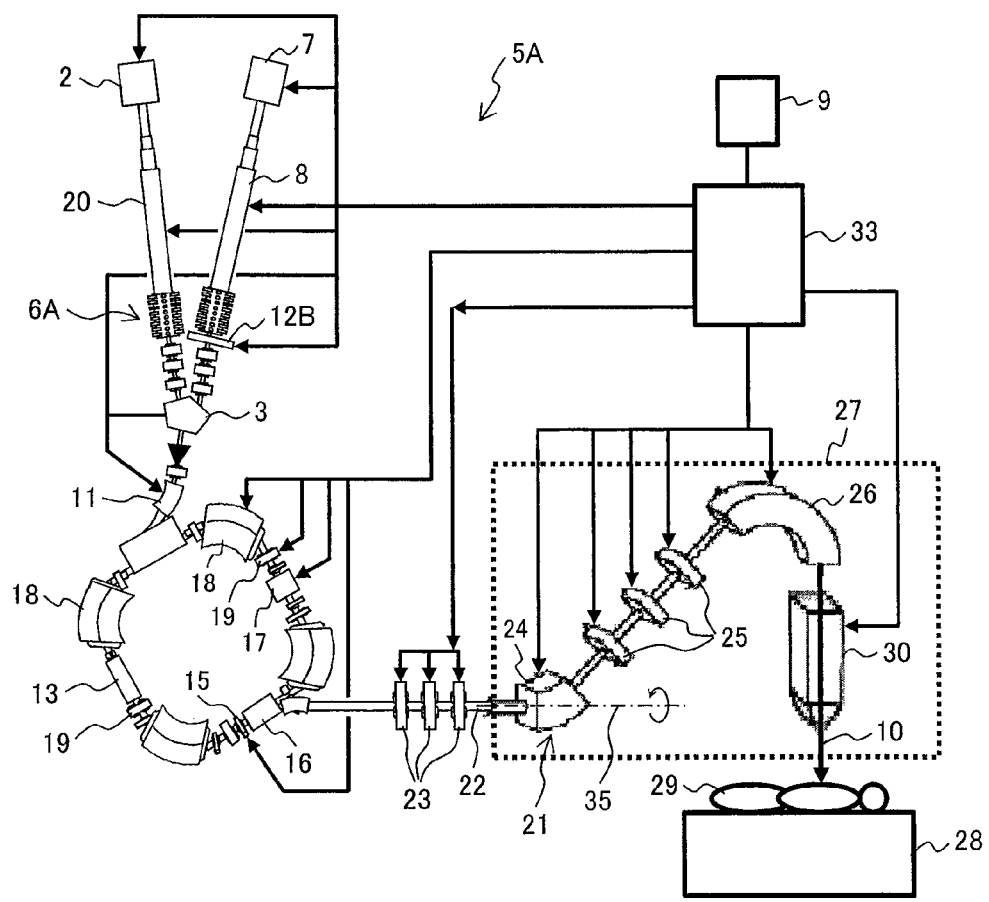
FIG. 12 is an enlarged structural diagram showing a charged particle beam system according to embodiment 4 which is other preferred embodiment of the present invention.

A charged particle beam irradiating method according to embodiment 4 which is other preferred embodiment of the present invention will be explained below. In the charged particle beam irradiating method of the present embodiment, a charged particle beam system 5A shown in FIG. 12 is used.

The charged particle beam system 5A is provided with a charged particle generator 6A, the beam transport system 21, the rotating gantry 27, the irradiation nozzle 30, and the control apparatus 33. The charged particle generator 6A includes a helium ion source 2 ($He^{2+}$), a carbon ion source 7 ($C^{4+}$), the linear accelerator 20 and a linear accelerator 8, a charge converter 12B for charge-converting carbon ions ($C^{4+}$) to carbon ions $C^{6+}$, and the switching magnet 3 in addition to the synchrotron accelerator 13. The helium ion source 2 is connected to the linear accelerator 20 and the carbon ion source 7 is connected to the linear accelerator 8. The switching magnet 3 switches the injection of the helium ion beam extracted from the linear accelerator 20 and the carbon ion ($C^{6+}$) beam extracted from the linear accelerator 8 to the circular beam duct of the synchrotron accelerator 13. The respective structures of the synchrotron accelerator 13, the beam transport system 21, the rotating gantry 27, and the irradiation nozzle 30 are the same as that of the charged particle beam system 5.

Either the helium ion beam extracted from the linear accelerator 20 or the carbon ion ($C^{6+}$) beam extracted from the linear accelerator 8 is injected to the synchrotron accelerator 13 by switching by the switching magnet 3. The ion beam (the helium ion beam or the carbon ion ($C^{6+}$) beam) injected to the synchrotron accelerator 13 is accelerated similarly to embodiment 1 and is extracted to the beam path 22 of the beam transport system 21. The extracted ion beam is scanned by the scanning magnets 32a and 32b in the irradiation nozzle 30 and the predetermined positions of a tumor volume 40B (refer to FIG. 13) is irradiated with the scanned ion beam.

In the synchrotron accelerator 13, the helium ion beam and the carbon ion beam are accelerated by the high-frequency acceleration apparatus 17 up to the maximum energy of 220 MeV per a nucleon (magnetic rigidity 4.5 Tm). By doing this, the helium ion beam becomes a longest underwater range of 30 cm and the carbon ion beam becomes a longest underwater range of 10 cm.

The dose monitors 52a and 52b in the irradiation nozzle 30 successively confirm the respective irradiation amounts by the helium ion beam and by the carbon ion beam. The helium ion beam (or the carbon ion beam) is scanned in the lateral direction by the scanning magnets 32a and 32b according to the shape of the irradiation target and the tumor volume 40B is irradiated with the helium ion beam (or the carbon ion beam). In the depth direction of the tumor volume 40B, the acceleration energy of the helium ion beam (or the carbon ion beam) is changed and the Bragg peak depth and the underwater range of the ion beam are changed.

Figure 13:
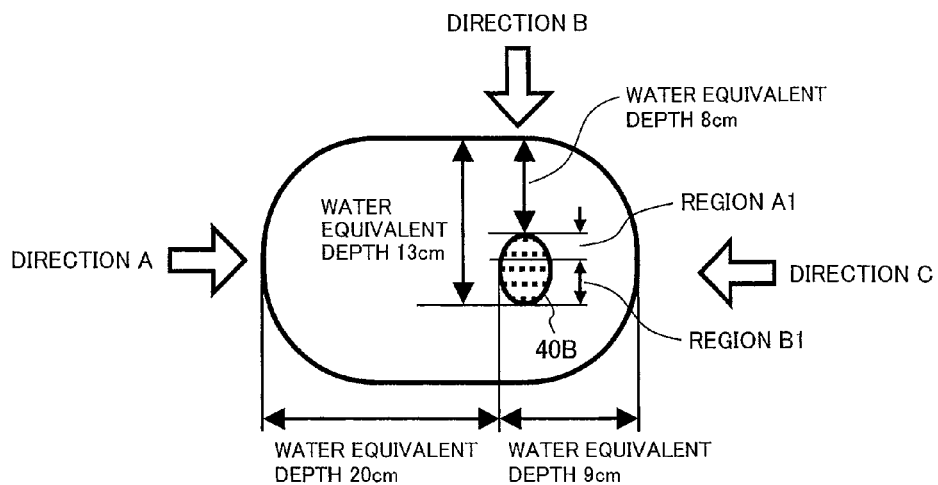
FIG. 13 is an explanatory drawing showing a state where an irradiation target is irradiated with ion beams in a charged particle beam irradiating method in which a charged particle beam system shown in FIG. 12 is used.

In the present embodiment, a tumor volume 40B exists in the position shown in FIG. 13 in the body of the patient 29 and the ion beam is irradiated with the tumor volume 40B in the 3 directions A, B, and C. Prior to treatment, the tumor volume 40B is imaginarily divided into the minute volume elements 41 by the treatment planning similarly to FIG. 4.

In the irradiation from the irradiation direction A, the water equivalent depth of the entire tumor volume 40B is 10 cm or larger and all the volume elements 41 is irradiated with the helium ion beam. The energy of the helium ion beam necessary for the irradiation to each volume element 41 and the irradiation amount thereof are beforehand determined by the treatment planning. The rotating gantry 31 is set at the angle beforehand determined by the treatment planning, and the helium ion beam is accelerated up to the energy for obtaining the underwater range suitable for the water equivalent depth of each volume element 41. The irradiation position in the lateral direction is adjusted by the scanning magnets 32a and 32b of the irradiation nozzle 30 and each volume element 41 is irradiated with the helium ion beam for the planned amount. After the volume element 41 is irradiated with the helium ion beam for the planned amount, the irradiation of the helium ion beam is stopped. When the water equivalent depth of the volume element 41 where is irradiated next with the helium ion beam is the same, the strength of the scanning magnets 32a and 32b is changed and the next volume element 41 is irradiated with the helium ion beam, and when the water equivalent depth of in the position of next volume element 41 is different, the acceleration energy of the helium ion beam is changed, and the irradiation position of the helium ion beam in the lateral direction is set by the scanning magnets 32a and 32b, and the irradiation of the ion beam is executed repeatedly. As a consequence, the irradiation of the ion beam to all the target volume is executed.

In the irradiation from the direction B, the depth of each volume element is within a range from a water equivalent depth of 8 cm to 13 cm and each volume element within a range from a water equivalent depth of 10 cm to 13 cm is irradiated with the helium ion beam. The volume elements 41 at a water equivalent depth of 8 cm to 10 cm are irradiated with the carbon ion beam. In the case of the irradiation from the direction C, the depth of each volume element 41 is 10 cm or lower and each volume element 41 within the range is irradiated with the carbon ion beam.

In the above embodiment, when the water equivalent depth is 10 cm or lower, any volume element 41 is irradiated with the carbon ion beam. However, each volume element 41 can be irradiated with the helium ion beam or carbon ion beam even when the water equivalent depth is 10 cm or lower. In this way, a high dose concentration and high dose distribution controllability are obtained and the irradiation time can be shortened.

In the present embodiment, the linear accelerator 12 and the synchrotron accelerator 13 are used as an accelerator. However, by using the cyclotron accelerator 55 as an accelerator and a helium ion source ($He^{2+}$) and a carbon ion source ($C^{6+}$) as an ion source to accelerate the ions up to energy of 220 MeV/a nucleon as shown in FIG. 14, installing a metallic degrader 56 for permitting the respective ion beams to pass through in the beam transport system 21, and changing the thickness of the degrader 56 to control the attenuation amount of the ion beam energy, a similar system to embodiment 4 can be realized.

When performing switching between the helium ion beam and the carbon ion beam, the polarity of the switching magnet 3 shown in FIG. 14 is changed, and the resonance frequency of the high-frequency accelerator 58 of the cyclotron accelerator 55 and the applied high-frequency are controlled. As a consequence, the ion beam is accelerated to a predetermined energy.

In the present embodiment, the irradiation target is irradiated with the helium ion beam and the carbon ion beam. However, by adding a proton ion source and a proton linear accelerator to the present embodiment, accelerating the ion beams up to 220 MeV by the synchrotron accelerator, and adding the irradiation of the proton ion beam to the irradiation of the helium ion beam and carbon ion beam, the irradiation time can be shortened while enhancing the dose concentration to the irradiation target.

REFERENCE SIGNS LIST

1: hydrogen molecule ion source, 2: helium ion source, 3: switching magnet, 5, 5A: charged particle beam system, 6, 6A: charged particle beam generator, 7: 8, 20: linear accelerator, 12, 12B: charge convertor, 13: synchrotron accelerator, 15: extraction high-frequency electrode, 16: extraction deflector, 17: high-frequency acceleration apparatus, 18, 24, 26: bending magnet, 19, 23, 25: quadrupole magnet, 21: beam transport system, 27: rotating gantry, 30, 30A: irradiation nozzle, 32a, 32b: scanning magnet, 33: control apparatus, 52a, 52b: irradiation amount monitor, 54: range compensator, 55: cyclotron accelerator, 56: degrader.

What is claimed is:

1. A charged particle beam system comprising:
an ion source generating a plurality of different kinds of ions differing in weight from each other;
an accelerator accelerating the ions generated in the ion source and that includes a plurality of magnets;
a beam transport system transporting an ion beam extracted from the accelerator; and
an irradiation nozzle irradiating the ion beam to an irradiation target;
a rotating gantry that rotates the irradiation nozzle around the irradiation target; and
a control apparatus configured to control the rotating gantry, the irradiation nozzle, and the accelerator to select which of the different kinds of ions are irradiated from the irradiation nozzle from a plurality of different irradiation directions based on a water equivalent depth of the irradiation target at each of the irradiation directions, and
wherein the control apparatus is configured to control respective magnetic field strengths of the magnets when accelerating the different kinds of ions at a radius along a circular track, and the accelerator accelerates a first kind of the ions to a first maximum energy and accelerates a second kind of the ions to a second maximum energy, and
wherein the control apparatus is further configured to set, the first maximum energy and the second maximum energy such that a first magnetic rigidity of the accelerator for accelerating the first kind of ions to the first maximum energy and a second magnetic rigidity of the accelerator for accelerating the second kind of ions to the second maximum energy are approximately equal.

2. The charged particle beam system according to claim 1, wherein the irradiation nozzle is installed in the rotating gantry,
wherein the control apparatus is configured to control the accelerator to accelerate the plurality of different kinds of ions so that an underwater range at a highest energy after acceleration is different in each species of the ions, and wherein the water equivalent depth of the irradiation target in a first one of the irradiation directions is equal to or less than the underwater range at the highest energy after the acceleration of the first kind of ions, and wherein the selected ions are transported to the irradiation nozzle using the ion source, the accelerator, the beam transport system, and the rotating gantry, thereby irradiating the irradiation target with the selected ions from the irradiation nozzle.

3. The charged particle beam system according to claim 2, wherein the control apparatus is configured to compare the water equivalent depth of each of a plurality of layers of the irradiation target divided in a depth direction in the irradiation target with a longest underwater range of each of the different kinds of ions, and wherein the control apparatus is configured to, for each of the layers and for each of the different irradiation directions, select the first kind of ions to be irradiated when the water equivalent depth of the respective layer is greater than 4 cm from a surface in the respective irradiation direction and select the second kind of ions to be irradiated when the water equivalent depth of the respective layer is equal to or less than 4 cm from the surface in the respective irradiation direction.

4. The charged particle beam system according to claim 2, wherein the irradiation nozzle includes a scanning magnet, wherein the control apparatus is configured to control an irradiation position and irradiation range of the ions from the irradiation nozzle in a lateral direction by controlling the scanning magnet based on a position and a range in the lateral direction of each of a plurality of volume elements of the irradiation target, and wherein the control apparatus is configured to, for each of the volume elements and for each of the different irradiation directions, select the first kind of ions to be irradiated when the water equivalent depth of the respective volume element is greater than 4 cm from a surface in the respective irradiation direction and select the second kind of ions to be irradiated when the water equivalent depth of the respective volume element is equal to or less than 4 cm from the surface in the respective irradiation direction.

5. The charged particle beam system according to claim 1, wherein the irradiation nozzle is installed in the rotating gantry, wherein the control apparatus is configured to control the accelerator to accelerate the plurality of different kinds of ions so that an underwater range after acceleration of a heaviest kind of the ions to a highest energy is shorter than an underwater range after acceleration of ions other than the heaviest kind of the ions to a highest energy.

6. The charged particle beam system according to claim 1, wherein the irradiation nozzle is installed in the rotating gantry, wherein the control apparatus is configured to control the accelerator to accelerate the plurality of different kinds of ions so that an underwater range of a heaviest kind of the ions after acceleration to a highest energy is shorter than an underwater range after acceleration of ions lighter than said heaviest kind of the ions after acceleration to a highest energy.

7. The charged particle beam system according to claim 1, wherein the irradiation nozzle is installed in the rotating gantry, wherein the control apparatus is configured to control the accelerator to accelerate each of the plurality of different kinds of ions so that an underwater range after accelerating the different kinds of ions to a highest energy decreases in correspondence with an increase in ion weight thereof, wherein the selected ions are transported to the irradiation nozzle using the ion source, accelerator, beam transport system, and rotating gantry, thereby irradiating the irradiation target with the selected ions from the irradiation nozzle.

8. The charged particle beam system according to claim 1, wherein the first kind of ions are selected and irradiated from a first one of the irradiation directions when the water equivalent depth of the irradiation target is greater than 4 cm, and the second kind of ions are selected and irradiated from a second one of the irradiation directions when the water equivalent depth of the irradiation target is equal to or less than 4 cm.

9. The charged particle beam system according to claim 8, wherein the first kind of ions are hydrogen ions and the second kind of ions are helium ions.

10. The charged particle beam system according to claim 1, wherein each of the first magnetic rigidity and the second magnetic rigidity is 4.5 Tm.

11. The charged particle beam system according to claim 1, wherein the control apparatus is configured to control the rotating gantry, the irradiation nozzle and the accelerator to select the first kind of ions to be irradiated from a second one of the irradiation directions for the water equivalent depth of the irradiation target that is greater than 4 cm, and thereafter select the second kind of ions to be irradiated from the second one of the irradiation directions for the water equivalent depth of the irradiation target that is equal to or less than 4 cm.

12. The charged particle beam system according to claim 1, wherein the first kind ions are selected and irradiated from a first one of the irradiation directions when the water equivalent depth of the irradiation target is greater than or equal to 10 cm, and the second kind of ions are selected and irradiated from a second one of the irradiation directions when the water equivalent depth of the irradiation target is less than 10 cm.

13. The charged particle beam system according to claim 12, wherein the first kind of ions are helium ions and the second kind of ions are carbon ions.

14. The charged particle beam system according to claim 12, wherein each of the first magnetic rigidity and the second magnetic rigidity is 4.5 Tm.

15. The charged particle beam system according to claim 12, wherein the control apparatus is configured to control the rotating gantry, the irradiation nozzle and the accelerator to select the first kind of ions to be irradiated from the second one of the irradiation directions for the water equivalent depth of the irradiation target that is greater than or equal to 10 cm, and thereafter select the second kind of ions to be irradiated from the second one of the irradiation directions for the water equivalent depth of the irradiation target that is less than 10 cm.

16. The charged particle beam system according to claim 1, wherein the first magnetic rigidity of the accelerator for accelerating the first kind of ions to the first maximum energy of 220 MeV and the second magnetic rigidity of the accelerator for accelerating the second kind of ions to the second maximum energy of 69 MeV are approximately equal.

17. The charged particle beam system according to claim 1, wherein the first magnetic rigidity of the accelerator for accelerating the first kind of ions to the first maximum energy and the second magnetic rigidity of the accelerator for accelerating the second kind of ions to the second maximum energy are approximately ½ of a third magnetic rigidity for obtaining a water equivalent depth of 30 cm for the second kind of ions.

* * * * *